United States Patent
Aizawa et al.

(10) Patent No.: US 9,260,656 B2
(45) Date of Patent: Feb. 16, 2016

(54) FLUORESCENT SILICA NANO-PARTICLE, FLUORESCENT NANO-MATERIAL, AND BIOCHIP AND ASSAY USING THE SAME

(75) Inventors: Hideki Aizawa, Tokyo (JP); Michio Ohkubo, Tokyo (JP); Michihiro Nakamura, Tokushima (JP); Hirokazu Miyoshi, Tokushima (JP)

(73) Assignees: THE FURUKAWA ELECTRIC CO., LTD., Tokyo (JP); THE UNIVERSITY OF TOKUSHIMA, Tokushima-shi (JP)

( * ) Notice: Subject to any disclaimer, the term of this patent is extended or adjusted under 35 U.S.C. 154(b) by 1766 days.

(21) Appl. No.: 11/898,787

(22) Filed: Sep. 14, 2007

(65) Prior Publication Data

US 2008/0293584 A1 Nov. 27, 2008

Related U.S. Application Data

(63) Continuation of application No. PCT/JP2006/325562, filed on Dec. 21, 2006.

(30) Foreign Application Priority Data

Dec. 27, 2005 (JP) ................................. 2005-376401

(51) Int. Cl.

| C12Q 1/00 | (2006.01) |
|---|---|
| C09K 11/06 | (2006.01) |
| B82Y 30/00 | (2011.01) |
| C12Q 1/68 | (2006.01) |
| C40B 70/00 | (2006.01) |
| G01N 33/533 | (2006.01) |
| G01N 33/552 | (2006.01) |
| G01N 33/58 | (2006.01) |
| C09B 11/24 | (2006.01) |
| C09B 23/04 | (2006.01) |
| C09B 23/06 | (2006.01) |
| C09B 67/08 | (2006.01) |
| C09B 67/00 | (2006.01) |

(52) U.S. Cl.
CPC .............. C09K 11/06 (2013.01); B82Y 30/00 (2013.01); C09B 11/24 (2013.01); C09B 23/04 (2013.01); C09B 23/06 (2013.01); C09B 67/0005 (2013.01); C09B 68/443 (2013.01); C12Q 1/6834 (2013.01); C40B 70/00 (2013.01); G01N 33/533 (2013.01); G01N 33/552 (2013.01); G01N 33/587 (2013.01); *B01J 2219/005* (2013.01); *B01J 2219/00576* (2013.01); *C12Q 1/6837* (2013.01)

(58) Field of Classification Search
None
See application file for complete search history.

(56) References Cited

U.S. PATENT DOCUMENTS

| 6,238,931 B1 | 5/2001 | Buechler et al. |
|---|---|---|
| 6,461,827 B1* | 10/2002 | Oda et al. ...................... 435/7.92 |
| 2003/0045717 A1* | 3/2003 | Czerney et al. ............... 544/300 |
| 2004/0014060 A1* | 1/2004 | Hoheisel et al. .................. 435/6 |
| 2004/0053222 A1 | 3/2004 | Storhoff et al. |
| 2004/0101822 A1* | 5/2004 | Wiesner et al. ..................... 435/5 |
| 2005/0147974 A1* | 7/2005 | Muller-Shulte ................... 435/6 |

FOREIGN PATENT DOCUMENTS

| JP | 8-503994 A | 4/1996 |
|---|---|---|
| JP | 2005-528466 A | 9/2005 |
| JP | 2005-532456 A | 10/2005 |

OTHER PUBLICATIONS

Zhao et al (2003 JACS 125:11474-5).*
Makrgiorgos et al (2002 Nature Biotechnology 20:936-9).*
Wang et al (2005 Nanoletters 5:37-43; published on the web Dec. 2, 2004).*
Ow, H., et al., Nano Letters, vol. 5, No. 1, pp. 113-117, (2005).
Smith, T.A., et al., Colloid & Polymer Science, vol. 276, No. 11, pp. 1032-1037, (1998).
Tleugabulova, D., et al., Langmuir, vol. 20, pp. 848-854, (2004).
Imhof, A., et al., J. Phys. Chem. B., vol. 103, No. 9, pp. 1408-1415, (1999).
Wang, L., et al., Nano Letters, vol. 5, No. 1, pp. 37-43, (2005).

* cited by examiner

*Primary Examiner* — Christopher M Gross
(74) *Attorney, Agent, or Firm* — Birch, Stewart, Kolasch & Birch, LLP (57) ABSTRACT

Colloidal silica particles containing a fluorescent dye compound, composed of a silica particle containing a silica component and a fluorescent dye compound chemically bound or adsorbed thereto,
wherein the colloidal silica particles containing a fluorescent dye compound have an average diameter of 30 nm or less, and wherein said silica particles are used simultaneously as fluorescent-labelling nanobeads; a fluorescent nano-material comprising said colloidal silica particles; and a biochip and an assay method using the same.

19 Claims, 2 Drawing Sheets

FLUORESCENT SILICA NANO-PARTICLE, FLUORESCENT NANO-MATERIAL, AND BIOCHIP AND ASSAY USING THE SAME

This application is a Continuation of co-pending PCT International Application No. PCT/JP2006/325562 filed on Dec. 21, 2006, which designated the United States, and on which priority is claimed under 35 U.S.C. §120. This application also claims priority under 35 U.S.C. §119(a) on Patent Application No(s). 2005-376401 filed in Japan on Dec. 27, 2005. The entire contents of each of the above documents is hereby incorporated by reference.

TECHNICAL FIELD

The present invention relates to colloidal silica particles containing a fluorescent dye compound, a fluorescent nano-material such as fluorescent-labelling nanobeads using the same, a biochip using the same, and a biomolecule-detecting and quantifying method using the same.

BACKGROUND ART

A diagnostic technique of using a biochip is attracting attention in advanced medical fields such as tailor-made medical practice and early diagnosis. The biochip generically designates devices carrying, as a capturing molecule, a biomolecule or a bioactive substance, such as antigen, antibody, DNA, RNA, sugar, polysaccharide, ligand, receptor, peptide, or chemical substance, arrayed and immobilized on a substrate.

A typical example of the biochip is a DNA chip. The DNA chip is aimed at detecting and quantifying a gene by allowing a DNA immobilized on a substrate to react with an analyte DNA or RNA and thus, detecting the fluorescence label introduced to the analyte DNA or RNA.

However, biochips including the DNA chip are lower for the reproducibility of the data obtained because of easier photobleaching (color-fading) of the dye used for fluorescence labeling. Therefore, there is a problem that the data obtained is still unsatisfactory in reliability for clinical applications.

Semiconductor nanoparticles such as CdSe have been known as fluorescent dyes resistant to the photobleaching. However, such semiconductor nanoparticles show fluorescence characteristics significantly different from those of the dye widely used for DNA chips currently such as Cy3 and Cy5, and thus it is difficult to apply such nanoparticles to the DNA chip analyzers currently used widely. In addition, when an analyte DNA is fluorescent-labelled or a DNA on a substrate is hybridized, it is difficult to remove semiconductor nanoparticles which have not labelled the analyte DNA fluorescently or semiconductor nanoparticle-labelled DNAs which have not been hybridized with the analyte DNA.

Thus, there are still these problems remaining in applying semiconductor nanoparticles to DNA chips.

Fluorescence silica particles containing an organic dye inside a silica particle are reported as a method of stabilizing the organic dye (see, for example, Non-patent Documents 1 to 3).

However, fluorescence silica particles so far reported, which had a particle diameter of at least approximately 30 nm. Therefore, there are problems that they did not allow efficient fluorescence labelling for use as a DNA chip dye, gave insufficient fluorescent intensity because of low integration of the fluorescent dye, and were vulnerable to photobleaching.

Non-patent Document 1: J. Phys. Chem. B 1999, 703, 1408-1415
Non-patent Document 2: Nano Letters 2005, 5, 113
Non-patent Document 3: Nano Letters 2005, 5, 37

DISCLOSURE OF INVENTION

For solving the above-mentioned problems, the present invention contemplates providing a group of colloidal silica particles containing a fluorescent dye compound simultaneously used as fluorescent-labelling nanobeads, colloidal silica particles containing a fluorescent dye compound used for a biochip as fluorescent-labelling nanobeads that having more brightness and that are more resistant to fluorescence photobleaching than a free fluorescent dye compound, a fluorescent nano-material comprising the colloidal silica particles, and a biochip and a method of detecting and quantifying a biomolecule using the silica particles.

According to the present invention, there is provided the following means:

(1) Colloidal silica particles containing a fluorescent dye compound, composed of a silica particle comprising a silica component and a fluorescent dye compound chemically bound or adsorbed thereto, wherein the colloidal silica particles containing a fluorescent dye compound have an average diameter of 30 nm or less;

(2) The colloidal silica particles containing a fluorescent dye compound according to the item (1), wherein at least one kind of the fluorescent dye compound is dispersed inside of each of the silica particles;

(3) The colloidal silica particles containing a fluorescent dye compound according to the item (1) or (2), wherein a fluorescence of the silica particles is yellow fluorescence, orange fluorescence or red fluorescence;

(4) The colloidal silica particles containing a fluorescent dye compound according to any one of the items (1) to (3), wherein the silica particles each have amino, hydroxyl, thiol, carboxyl, maleimide and/or succinimidyl ester groups on a surface of each of the particles;

(5) The colloidal silica particles containing a fluorescent dye compound according to any one of the items (1) to (4), wherein the surface of the silica particles is modified with a substance specifically binding to or adsorbed to a target biomolecule; and wherein a fluorescence of the silica particles that is resistant to photobleaching;

(6) The colloidal silica particles containing a fluorescent dye compound according to any one of the items (1) to (5), wherein the fluorescent dye compound is represented by any one of the following Formulae (1) to (3):

[Chemical formula 1]

Formula (1)

wherein each X independently represents $CR^3R^4$; each Y independently represents an atom or group selected from a hydrogen atom, hydrocarbon groups, and heteroatom-containing functional groups; either of $R^1$ or $R^2$ represents a group binding to the silica component covalently or a hydrocarbon group containing the group, and the other represents a hydrocarbon group that may have a functional group; each of $R^3$ and $R^4$ is a hydrogen atom or a hydrocarbon group, and at least one of them is a hydrocarbon group; and n is 1 or 2; and

[Chemical formula 2]

Formula (2)

Formula (3)

wherein, $R^{11}$ and $R^{21}$ each represent a group binding to the silica component covalently;

(7) The colloidal silica particles containing a fluorescent dye compound according to any one of the items (1) to (6), wherein the colloidal silica particles containing a fluorescent dye compound are used for a biochip as fluorescent-labelling nanobeads,
wherein the nanobeads increase brightness as compared with a free fluorescent dye compound; and
wherein a fluorescence of the nanobeads that is resistant to photobleaching;

(8) A fluorescent nano-material, comprising the colloidal silica particles containing a fluorescent dye compound according to any one of the items (1) to (7);

(9) A biochip, comprising the colloidal silica particles containing a fluorescent dye compound according to any one of the items (1) to (7) as fluorescent-labelling nanobeads,
wherein the nanobeads increase brightness as compared with a free fluorescent dye compound; and
wherein a fluorescence of the nanobeads that is resistant to photobleaching;

(10) A method of detecting or quantifying a biomolecule, comprising the steps of:
allowing a target biomolecule-recognizing molecule immobilized on a substrate to molecularly recognize a target biomolecule, allowing at least one of the colloidal silica particles containing a fluorescent dye compound according to any one of the items (1) to (7) surface-modified with a second substance molecularly recognizing a first molecular-recognition substance to molecularly recognize the target biomolecule after molecular recognition by the target biomolecule-recognizing molecule immobilized on the substrate, and
detecting or quantifying a fluorescence from the colloidal silica particles on the substrate; and
wherein the target biomolecule in a sample is modified with the first molecular-recognition substance;

(11) The method of detecting or quantifying a biomolecule according to the item (10), wherein the combination of the first molecular-recognition substance and the second substance is any one combination selected from the group consisting of the following items (a) to (i):
(a) the first molecular-recognition substance is an antigen and the second substance is an antibody;
(b) the first molecular-recognition substance is an antibody and the second substance is an antigen;
(c) the first molecular-recognition substance is biotin and the second substance is avidin or streptavidin;
(d) the first molecular-recognition substance is avidin or streptavidin and the second substance is biotin;
(e) the first molecular-recognition substance is a sugar or polysaccharide and the second substance is a sugar-binding protein binding to the sugar or polysaccharide specifically;
(f) the first molecular-recognition substance is a sugar-binding protein and the second substance is a sugar or polysaccharide binding to the protein specifically;
(g) the first molecular-recognition substance is a ligand and the second substance is a receptor binding to the ligand specifically;
(h) the first molecular-recognition substance is a receptor and the second substance is a ligand binding to the receptor specifically; and
(i) the first molecular-recognition substance is a chemical substance and the second substance is an antibody or peptide binding to the substance specifically;

(12) A method of detecting or quantifying a biomolecule using a double antibody sandwich system, which comprises using, as a fluorescent-labelling antibody, the colloidal silica particles containing a fluorescent dye compound according to any one of the items (1) to (7) surface-modified with an antibody recognizing an antibody recognition site of a target biomolecule;

(13) A method of detecting or quantifying a biomolecule, comprising the steps of:
labelling a target biomolecule in a sample with the colloidal silica particles containing a fluorescent dye compound according to any one of the items (1) to (7),
allowing a target biomolecule-recognizing molecule immobilized on a substrate to molecularly recognize the target biomolecule labelled with the colloidal silica particles, and
detecting or quantifying a fluorescence form the colloidal silica particles on the substrate;

(14) The method of detecting or quantifying a biomolecule according to any one of the items (10) to (13), wherein the target biomolecule is an antigen, an antibody, a DNA, a RNA, a sugar, a polysaccharide, a ligand, a receptor, a peptide or a chemical substance;

(15) A method of detecting or quantifying a DNA or RNA, comprising the steps of:
labelling a target DNA or RNA in a sample with the colloidal silica particles containing a fluorescent dye compound according to any one of the items (1) to (7), allowing the above-labelled target DNA or RNA to hybridize with a DNA or RNA immobilized on a substrate, and detecting or quantifying a fluorescence label signal from the colloidal silica particles on the substrate; and (16) The method of detecting or quantifying a biomolecule according to any one of the items (10) to (15), wherein two or more kinds of target biomolecules are detected or quantified simultaneously.

In the present description and the claims thereof, the biochip (bioelement) means a solid substrate on which a biomolecule (including a bioactive substance, the same shall apply hereinafter) arrayed and immobilized on a substrate as described above is brought into contact with another biomolecule or compound and the resulting specific interaction is detected or quantified by the change in optical, electrical or physical signal, and a detecting means for that purpose. Examples thereof include a DNA chip, a protein chip and the like.

Also, in the present description and the claims thereof, the phrase "at least one kind of fluorescent dye compounds is dispersed inside of a whole silica particle" means that at least one kind of fluorescent dye compounds is immobilized at high concentration in the silica particle, and the concentration of the fluorescent dye compound(s) in the silica particle is preferably 35 to 75 mmol/L, more preferably 40 to 55 mmol/L.

The "concentration fluorescent dye compound(s) in the silica particle" is a value calculated by dividing the molar number of the fluorescent dye compounds by the volume of the colloidal silica particles containing a fluorescent dye compound. The molar number of the fluorescent dye compound(s) is determined from the light absorbance of the colloidal silica particles dispersion containing the fluorescent dye compound, and the volume of the colloidal silica particles containing the fluorescent dye compound is a value obtained by determining the size and thus the volume of the silica particle from TEM micrograph or by determining the mass of light-absorbing silica particles by collecting, drying, and weighing them only from the colloidal silica particles dispersion containing the fluorescent dye compound and dividing the mass by an apparent density of silica particle of 2.3 g/cm$^3$.

The "fluorescence" in the present invention is not differentiated from phosphorescence, and thus is the fluorescence in the broader sense including phosphorescence. Thus in the present invention, the fluorescence lifetime is not particularly limited, and thus, the emission fluorescence lifetime may be $10^{-3}$ second to 1 day or more, preferably $10^{-10}$ second to $10^{-1}$ second, more preferably $10^{-9}$ second to $10^{-3}$ second, and still more preferably $10^{-9}$ second to $10^{-5}$ second.

The "fluorescence", which is light emission at the wavelength inherent to the fluorescent dye compound, is a phenomenon different from light absorption defined by the difference in light intensity between the incident light and the outgoing light from a light-absorbing substance. Accordingly, the light to be analyzed and also the measurement system such as analytical mechanism are different between fluorescence and light absorption.

In the present invention, the phrase "a fluorescence is resistant to photobleaching" means that a degree of the decay in fluorescence intensity of the colloidal silica particles containing a fluorescent dye compound when a dispersion thereof is irradiated by an argon lamp for 30 minutes is 20% or less of that of the decay in fluorescence intensity of the fluorescent dye compound (for example, fluorescein) in a solution at the same concentration.

A free fluorescent dye compound performs one fluorescence labelling per molecule, while a group of fluorescent dye compounds of at least one kind dispersed inside the silica particle of the present invention perform fluorescence labelling in a body.

Other and further features and advantages of the invention will appear more fully from the following description, appropriately referring to the accompanying drawings.

BEST MODE FOR CARRYING OUT THE INVENTION

The colloidal silica particles containing a fluorescent dye compound of the present invention will be described first.

The colloidal silica particles containing a fluorescent dye compound of the present invention are a plurality of colloidal silica particles, composed of a silica particle comprising a silica component and a fluorescent dye compound chemically bound or adsorbed thereto, wherein the colloidal silica particles containing the fluorescent dye compound have an average diameter of 30 nm or less that label a target biomolecule (including a bioactive material) with a fluorescent label, and wherein the fluorescent dye compound is dispersed inside of each of the particles.

The fluorescent dye compound is preferably dispersed inside of the whole silica particle, both inside and in the region close to the surface, and more preferably in the silica particle from the center to the surface.

The colloidal silica particle of the present invention has different features from a colloidal silica particle having a core shell structure, because the fluorescent dye compound is dispersed in the region close to the surface or at the surface.

The colloidal silica particles containing a fluorescent dye compound of the present invention may be used as a fluorescent nano-material.

The fluorescent nano-material of the present invention that comprises the colloidal silica particles containing a fluorescent dye compound is superior in brightness and fluorescence photobleaching resistance.

The fluorescent nano-material of the present invention may be used as fluorescent-labelling nanobeads labelling a target biomolecule with a fluorescent label, a cosmetic material, or the like.

In addition in the present invention, a fluorescent nano-material may be formed by using multiple kinds of the colloidal silica particles containing a fluorescent dye compound together as fluorescent-labelling nanobeads.

The "adsorption" above is binding by Van der Waals force or hydrophobic interaction.

Examples of the target biomolecule or the target bioactive substance include antigens, antibodies, DNAs, RNAs, sugars, polysaccharides, ligands, receptors, peptides, chemical substances and the like.

In the present description and its claims, the term "ligand" means a substance specifically bonding to a protein, and examples thereof include substrates binding to enzyme, coenzymes, regulatory factors, hormones, neurotransmitters, and the like, and thus, the ligands include low-molecular weight molecules as well as high-molecular weight substances.

The chemical substances include not only natural organic compounds but also bioactive compounds artificially prepared, environmental hormones, and the like.

Hereinafter, the fluorescent dye compound for use in the present invention will be described.

As described above, the fluorescent dye compound for use in the present invention is a fluorescent dye compound in the broader sense, and may comprise a phosphorescent dye compound.

The fluorescent dye compound for use in the present invention may have an additional label other than the fluorescent label such as magnetic label, radioactive label, or pH-sensitive-dye label.

In addition to the fluorescent dye compound, a labelling compound other than the fluorescent dye compound may be added to the colloidal silica particle containing the fluorescent dye compound of the present invention.

Examples of the labelling compounds to be added together with the fluorescent dye compound include magnetic compounds, radioactive labelling compounds, pH-sensitive dye compounds, and the like.

It is thus possible to detect a target biomolecule labelled with the colloidal silica particles containing a fluorescent dye compound of the present invention twice or more with fluorescence and also with the other labels, by using a fluorescent dye compound having a label other than the fluorescent label in the colloidal silica particles containing a fluorescent dye compound of the present invention or by using a fluorescent dye compound and other labelling compounds in the colloidal silica particles containing the fluorescent dye compound of the present invention. It is thus possible to improve the efficiency in separating and purifying the target biomolecule and the accuracy in quantitative determination.

The fluorescent dye compound is not particularly limited, but, to be used for a DNA chip, it is preferably a fluorescent dye compound having an excitation wavelength and an emission wavelength similar to those of Cy3 or Cy5 represented by the following Formula (1) (trade name, manufactured by Amersham Biosciences K.K.), from the viewpoint of compatibility as to detection and data in general purpose detectors, so-called chip readers (for example, DNA microarray scanner manufactured by Agilent Technologies Japan, Ltd. and ScanArray series products manufactured by PerkinElmer Japan Co., Ltd.).

[Chemical formula 3]

Formula (1)

wherein each X independently represents $CR^3R^4$; each Y independently represents an atom or group selected from a hydrogen atom, hydrocarbon groups, and heteroatom-containing functional groups; either of $R^1$ or $R^2$ represents a group binding to the silica component covalently or a hydrocarbon group having 1 to 10 carbon atoms and containing the group, and the other represents a hydrocarbon group having 1 to 10 carbon atoms that may have a functional group; each of $R^3$ and $R^4$ is a hydrogen atom or a hydrocarbon group, and at least one of them is a hydrocarbon group; and n is 1 or 2.

Specifically, in the Formula (1), $X(CR^3R^4)$ represents $CH(CH_3)$, $C(CH_3)_2$, $C(CH_3)(C_2H_5)$, or the like. Examples of Y include a hydrogen atom, alkyl groups such as methyl, ethyl, propyl, and butyl; aryl groups, a hydroxyl group, a thiol group, an amino group, a cyano group, a nitro group, a sulfone group, a carboxyl group, alkylcarbonyl groups, and the like. Examples of the group binding to the silica component covalently represented by $R^1$ or $R^2$ include active ester groups such as NHS (N-hydroxysuccinimide) ester group, a maleimide group, an isothiocyanate group, an isocyanate group, a cyano group, an aldehyde group, and the like, and these groups bind to the silica component having amino, thiol, and other groups covalently, forming amide, thioester, urea, thiourea, or other bonds. Examples of the hydrocarbon group that may have a functional group represented by $R^1$ or $R^2$ include ethyl and benzyl groups and the like.

The Cy3 or Cy5 is preferably represented by the following Formula, respectively:

[Chemical formula 4]

In the Formula, $R^5$, $R^6$, $R^7$, and $R^8$ each represent a group binding to the silica component covalently, and examples thereof include active ester groups such as NHS ester group, a maleimide group, an isothiocyanate group, an isocyanate group, a cyano group, an aldehyde group and the like.

The fluorescent dye compound having an excitation wavelength and an emission wavelength similar to those of Cy3 is for example a compound having an excitation wavelength peak at 548 to 556 nm and an emission wavelength peak at 563 to 584 nm, and the fluorescence color of the colloidal silica particles containing a fluorescent dye compound of the present invention is, for example, yellow (540 to 590 nm) or orange (590 to 620 nm). Specific examples thereof include

DY550 and DY555 (trade names, manufactured by Dyomics GmbH), 5-TAMRA, BODIPY-TMR-X, Alexa Fluor546, and Alexa Fluor555 (trade names, manufactured by Invitrogen Corporation.) represented by the following Formulae and the like, and DY550 is preferable.

In the Formula, $R^{11}$, $R^{12}$, and $R^{13}$ each represent a group binding to the silica component covalently, and examples thereof include active ester groups such as NHS ester group, a maleimide group, an isothiocyanate group, an isocyanate group, a cyano group, an aldehyde group and the like.

The fluorescent dye compound having an excitation wavelength and an emission wavelength similar to those of Cy5 is for example a compound having an excitation wavelength peak at 636 to 654 nm and an emission wavelength peak at 657 to 679 nm, and the fluorescence color of the colloidal silica particles containing a fluorescent dye compound of the present invention is, for example, red (620 to 740 nm) or the like. Specific examples thereof include DY630, DY631, DY633, DY635, DY636, DY650, and DY651 (trade names, manufactured by Dyomics GmbH), BODIPY 630/650, Alexa Fluor633, and Alexa Fluor647 (trade names, manufactured by Invitrogen Corporation.), and Oyster643 and Oyster656 (trade names, manufactured by Denovo Biolabels GmbH) represented by the following Formulae, and the like.

DY635

DY636

DY650

[Chemical formula 7]

DY651

In the Formula, $R^{21}$, $R^{22}$, $R^{23}$, $R^{24}$, $R^{25}$, $R^{26}$, and $R^{27}$ each represent a group binding to the silica component covalently, and examples thereof include active ester groups such as NHS ester group, a maleimide group, an isothiocyanate group, an isocyanate group, a cyano group, an aldehyde group and the like.

Specific examples of the magnetic compounds, radioactive labelling compounds, and pH-sensitive dye compounds above include methyl viologen, xylenol orange, 4-amino-(2,3,6,6-tetramethyl-1-piperidinyloxy), 4-maleimide-(2,3,6,6-tetramethyl-1-piperidinyloxy), xylene cyanol, bromophenol blue and the like.

Hereinafter, a method of preparing the colloidal silica particles containing a fluorescent dye compound of the present invention will be described.

The colloidal silica particles containing a fluorescent dye compound of the present invention can be prepared by allowing a fluorescent dye compound to react with a silane compound, forming a chemical, covalent or ionic, bond, or to be adsorbed to the silane compound and polymerizing one or more silane compounds thereto.

The colloidal silica particles containing a fluorescent dye compound of the present invention is preferably prepared by allowing a fluorescent dye compound having an active group such as N-hydroxysuccinimide (NHS) ester group, a maleimide group, an isocyanate group, an isothiocyanate group, an aldehyde group, a para-nitrophenyl group, a diethoxymethyl group, an epoxy group, or a cyano group, to react with a silane-coupling agent having a substituent group reactive with the active group (such as amino group, hydroxyl group, or thiol group), forming a covalent bond and polymerizing one or more silane compounds on the product thus obtained.

The inventors have filed patent applications on a method of preparing fluorescent dye compound-containing colloidal silica particles (for example, Japanese Patent Application No. 2004-356608). The colloidal silica particles containing a fluorescent dye compound of the present invention are more preferably prepared according to the method. Specifically, the colloidal silica particles containing a fluorescent dye compound can be prepared in the following steps (a) and (b):

a step (a) of forming a dye/silane-coupling agent composite compound (3) in reaction of a fluorescent dye compound (1) containing an active ester group such as N-hydroxysuccinimide (NHS) ester with an amino group-containing silane-coupling agent (2), and a step (b) of polymerizing a silica compound (4) on the dye/silane-coupling agent composite compound (3) obtained in the step (a) under a basic condition.

The inventors have filed patent applications on the step of esterifying a carboxylic acid compound with N-hydroxysuccinimide (for example, Japanese Patent Application No. 2004-356608).

The NHS ester group-containing fluorescent dye compound (I) used in the step (a) may be prepared according to the esterification reaction step therein. However, a commercially available product may be used instead.

Specific examples of the NHS ester group-containing fluorescent dye compounds (I) include DY550-NHS ester, DY555-NHS ester, DY630-NHS ester, and DY635-NHS ester (trade names, manufactured by Dyomics GmbH), 5-TAMRA-NHS ester, Alexa Fluor546-NHS ester, Alexa Fluor555-NHS ester, Alexa Fluor633-NHS ester, and Alexa Fluor647-NHS ester (trade names, manufactured by Invitrogen Corporation.), Oyster643-NHS ester and Oyster656-NHS ester (trade names, manufactured by Denovo Biolabels GmbH), and the like. Among them, DY550-NHS ester and DY630-NHS ester represented by the following Formulae are preferable.

[Chemical formula 8]

DY550-NHS ester

[Chemical formula 9]

DY630-NHS ester

The amino group-containing silane-coupling agent (2) is not particularly limited, and examples thereof include γ-aminopropyltriethoxysilane (APS), 3-[2-(2-aminoethylamino) ethylamino]propyltriethoxysilane, N-2-(aminoethyl)-3-aminopropylmethyldimethoxysilane, and 3-aminopropyltrimethoxysilane. Among them, APS is preferable.

The reaction between the NHS ester group-containing fluorescent dye compound (1) and the amino group-containing silane-coupling agent (2) may be carried out, by dissolving the ingredients in a solvent such as DMSO (dimethylsulfoxide) or DMF (N,N-dimethylformamide) and stirring the mixture at room temperature (for example, 25° C.).

The ratio of the NHS ester group-containing fluorescent dye compound (1) to the silane-coupling agent (2) used in the reaction is not particularly limited, but the ratio of the NHS ester group-containing fluorescent dye compound (1) to the amino group-containing silane-coupling agent (2) is preferably 1:0.5 to 2 (molar ratio), more preferably 1:0.8 to 1.2 (molar ratio).

Thus, a dye/silane-coupling agent composite compound (3) can be obtained by reacting the carbonyl group in the fluorescent dye compound (1) with the amino group of the amino group-containing silane-coupling agent (2), thereby forming an amide bond (—NHCO—). In other words, a fluorescent dye compound and a silica component are bound to each other via an amide bond in the dye/silane-coupling agent composite compound (3).

In the subsequent step (b), the dye/silane-coupling agent composite compound (3) is allowed to react with a silica compound (4). The silica compound (4) is not particularly limited, and examples thereof include tetraethoxysilane (TEOS), γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, and 3-[2-(2-aminoethylamino)ethylamino]propyltriethoxysilane. Among them, TEOS, MPS, and APS are preferable.

The ratio of the dye/silane-coupling agent composite compound (3) to the silica compound (4) is not particularly limited, but the molar ratio of the silica compound (4) to one mole of the dye/silane-coupling agent composite compound (3) is preferably 50 to 40,000, more preferably 100 to 2,000, and still more preferably 150 to 1,000.

The reaction is preferably carried out in the presence of alcohol, water, and ammonia. The alcohol is, for example, a lower alcohol having 1 to 3 carbon atoms such as methanol, ethanol, or propanol.

The ratio of water to alcohol in the reaction system is not particularly limited, but, the alcohol is used in an amount in the range of 0.5 to 20 parts, more preferably 2 to 16 parts, and still more preferably 4 to 10 parts by volume, with respect to one part of water by volume. The amount of ammonia is not particularly limited, but the ammonia concentration is preferably 30 to 1,000 mM, more preferably 60 to 500 mM, and still more preferably 80 to 200 mM.

The reaction may be carried out at room temperature, preferably as it is stirred. Generally, the colloidal silica particles containing a fluorescent dye compound of the present invention (5) can be prepared in a reaction period of several dozen minutes to several dozen hours.

The colloidal silica particles containing a fluorescent dye compound of the present invention that contains the fluorescent dye compound and additionally another labelling compound (for example, magnetic compound) can also be prepared by a method similar to that above.

It is possible to control the size (diameter) of the silica particles properly by adjusting the concentration of the silica compound (4) used and the reaction time in the step (b). It is also possible to prepare finer silica particles by lowering the concentration of the silica compound (4) used and shortening the reaction time (see, for example, Blaaderen et al., "Synthesis and Characterization of Monodisperse Colloidal Organo-silica Spheres", J. Colloid and Interface Science 156, 1-18. 1993). On the other hand, it is possible to prepare larger silica particles by repeating the step (b) plural times. It is thus possible to adjust the particle diameter of the colloidal silica particles containing the fluorescent dye compound obtained freely in a desirable range, for example, at the order of from nm order to μm. Specifically, it is possible to produce colloidal silica particles containing the fluorescent dye compound, having a small diameter of 3 to 30 nm. It is also possible as needed to make the particles have a desirable particle diameter distribution by an additional treatment, and thus to produce silica particle having a particle diameter distribution in a desirable range.

A group of the colloidal silica particles containing the fluorescent dye compound thus obtained may be purified as needed by a conventional method, for example by using an ultrafiltration membrane, for removal of copresent ions and impurities.

A group of spherical or almost spherical silica particles can be prepared by the method described above. Specifically, the almost spherical fine particle means a particle having a major axis/minor axis ratio of 2 or less.

The average diameter of the colloidal silica particles containing a fluorescent dye compound of the present invention is preferably 3 to 30 nm, more preferably 3 to 20 nm, and still more preferably 3 to 10 nm.

However, the colloidal silica particles above may be used as labelling particles for biochips even when the average diameter thereof is 3 nm or less, the diameter is preferably 3 nm or more, because the yield of the particles having a diameter of 3 nm or less is very low and thus the particles are more expensive.

Alternatively, particles having an average diameter of 30 nm or more lead to deterioration in accuracy of quantitative determination, because the particles are not reactive enough to react with all biological substances (e.g., target biomolecules) on the biochip because of steric hindrance.

Ratios of CV values, as determined by repeating a test of labelling the spots of a biomolecule in the same amount on a biochip with the colloidal silica particles containing a fluorescent dye compound and measuring the fluorescence intensity thereof four times, are summarized in Table 1. As is apparent from Table 1, the average diameter of the colloidal silica particles containing a fluorescent dye compound is preferably 3 to 30 nm, more preferably 3 to 20 nm, and still more preferably 3 to 10 nm, for more accurate quantitative determination.

[Table 1]

TABLE 1

| | Average diameter | | | |
| --- | --- | --- | --- | --- |
| | 4 nm | 12 nm | 27 nm | 45 nm |
| Quantitativity (Ratios of CV values) | 1 | 1.4 | 1.6 | 2.9 |

For obtaining silica particles having a desirable average diameter, it is possible to remove particles having a larger particle diameter by ultrafiltration by using an ultrafiltration film such as YM-10 or YM-100 (trade name, manufactured by Millipore Corporation).

In the present invention, the average diameter is an average diameter of the circle (average circle-equivalent diameter) obtained by measuring the total projected area of 50 randomly-selected silica particles for example in an image obtained under transmission electron microscope (TEM) or scanning electron microscope (SEM) using an image processing equipment, dividing the total area with the number of the silica particles (50), and determining the circle having an area equivalent to that.

The variation coefficient, so-called CV value, of the particle size distribution is not particularly limited, but preferably 10% or less, more preferably 8% or less.

In the present description and the claims thereof, a term "monodispersion" is used for particles having a CV value of 15% or less.

When immobilized and embedded in the silica particle, the fluorescent dye compound is dispersed inside the silica particle and thus, becomes more sensitive than its free fluorescent dye compound. It is thus possible to make the brightness thereof higher than that of the free fluorescent dye compound.

In addition, the colloidal silica particles containing a fluorescent dye compound of the present invention allows immobilization and embedding of more fluorescent dye compounds therein without self-quenching (see, for example, Japanese Patent Application No. 2004-356608). For that reason, it gives a high-sensitivity labelled product that can be used even in minute regions.

Hereinafter, surface modification of the colloidal silica particle will be described.

Generally, silica is known to be inactive chemically and easily modified. Any desirable molecule can also be bound to the surface of the colloidal silica particles containing a fluorescent dye compound of the present invention easily. Further, the surface of the colloidal silica particle containing a fluorescent dye compound of the present invention can be made the surface mesoporous or smooth.

Specifically according to the kind of the silica compound (4) used in the step (b), the colloidal silica particle containing a fluorescent dye compound of the present invention can be surface-modified to a colloidal silica particle containing a fluorescent dye compound having, on the surface, an acceptor group that can bind to a desirable molecule. The acceptor group is, for example, an amino, a hydroxyl, a thiol, a carboxyl, a maleimide, or a succinimidyl ester group.

The relationship between the silica compound (4) used in reaction and the acceptor group formed on the surface of the colloidal silica particle containing a fluorescent dye compound thus obtained are shown in Table 2.

[Table 2]

TABLE 2

| Silica compound (4) | Acceptor group formed on silica particle surface |
| --- | --- |
| Tetraethoxysilane | OH group |
| γ-Mercaptopropyltriethoxysilane | SH group |
| Aminopropyltriethoxysilane | $NH_2$ group |
| 3-Thiocyanato propyl triethoxysilane | SCN group |
| 3-Glycidyloxypropyltriethoxysilane | Epoxy group |
| 3-Isocyanato propyl triethoxysilane | CNO group |

If an acceptor group different from the acceptor group introduced on the surface of each of the colloidal silica particles containing a fluorescent dye compound (5) with the silica compound (4) used in the reaction is to be introduced, the colloidal silica particles containing a fluorescent dye compound (5) is treated additionally with a silica compound different from the silica compound (4) used in step (b). The treatment can be performed by an operation similar to that in step (b), by using a silica compound different from the silica compound (4) used in step (b).

The colloidal silica particles containing a fluorescent dye compound of the present invention allows binding to or adsorption on the surface and modification of a desirable molecule [such as antigen, antibody, DNA, RNA, sugar, polysaccharide, ligand, receptor, peptide, chemical substance, or the like], according to the kind of the acceptor group present on the surface.

The method of modifying the surface of the colloidal silica particles containing a fluorescent dye compound of the present invention with a desirable biomolecule or the like is not particularly limited, and examples thereof include the following methods (i) to (iii).

(i) Colloidal silica particles containing a fluorescent dye compound having thiol groups on the surface such as those prepared by using MPS or the like can be modified on the surface with a biomolecule or the like via a disulfide bond, a thioester bond, or a bond formed by thiol substitution reaction.

(ii) In particular when the biomolecule or the like has one or more amino groups, the thiol group on the colloidal silica particles containing a fluorescent dye compound and the amino group on the biomolecule or the like may be bound to each other, by using a crosslinking agent such as succinimidyl-trans-4-(N-maleimidylmethyl)cyclohexane-1-carboxylate (SMCC) or N-(6-maleimidocaproyloxy)succinimide (EMCS).

(iii) In the case of colloidal silica particles containing a fluorescent dye compound which have amino groups on the surface such as those prepared, for example, by using APS, the amino group thereof and the thiol group of the biomolecule or the like may be bound to each other by using a crosslinking agent such as SMCC or EMCS, as described above. Alternatively, the amino group on the particle and the amino group of the biomolecule or the like may be bound to each other by using a crosslinking agent such as glutaric aldehyde. Yet alternatively, the surface may be modified with a biomolecule or the like via an amide bond or a thiourea bond.

In the present invention, the colloidal silica particles containing a fluorescent dye compound may be modified directly with a target biomolecule, but preferably, the desirable molecule (such as antibody, DNA, RNA, sugar chain, receptor, peptide) that modifies the colloidal silica particles containing a fluorescent dye compound plays a role as an acceptor molecule and binds to a target biomolecule specifically in a specific molecularly recognizing reaction such as antigen-antibody reaction, biotin-avidin reaction, or hybridization using the complementarity of nucleotide sequences.

Alternatively when the target biomolecule is modified with a first molecular-recognition substance, the colloidal silica particles containing a fluorescent dye compound may be surface-modified with a second substance molecularly recognizing the first molecular-recognition substance, as will be described below in the section of a method of detecting or quantify a target biomolecule.

Herein, the molecularly recognizing reaction means a reaction proceeding by a specific interaction between biomolecules such as (1) hybridization between DNA's or between a DNA and a RNA, (2) antigen-antibody reaction, or (3) enzyme (receptor)-substrate (ligand) reaction.

Hereinafter, a set of multiple kinds of colloidal silica particles containing a fluorescent dye compound will be described.

In the present invention, use of multiple different kinds of colloidal silica particles containing a fluorescent dye compound as a set on a biochip described below allows simultaneously detection or quantitative determination of two or more target biomolecules.

The set of multiple kinds of the colloidal silica particles containing a fluorescent dye compound comprises two or more kinds of colloidal silica particles containing a fluorescent dye compound which contain different fluorescent dye compounds respectively surface-modified with different surface-modifying substance.

The surface-modifying substance may be a substance specifically binding to or being adsorbed to the target biomolecule, or a second substance molecularly recognizing a first molecular-recognition substance, when the target biomolecule is modified with the first molecular-recognition substance.

Typical examples of the set of multiple kinds of colloidal silica particles containing a fluorescent dye compound include a set of silica particles containing a yellow fluorescence compound (for example, DY550) surface-modified with a DNA that recognizes a target DNA, and silica particles containing a red fluorescence compound (for example, DY630) surface-modified with a ligand that recognizes a target protein. It is possible to detect or quantify a target DNA and a target protein simultaneously by using the set of particles on a biochip described below.

Hereinafter, the biochip of the present invention will be described.

The colloidal silica particles containing a fluorescent dye compound, wherein the fluorescence of the silica particles is resistant to photobleaching and the silica particles have higher brightness than the free fluorescent dye compound, can be used favorably on various biochips demanding high-sensitivity analysis.

The biochip of the present invention employs the colloidal silica particles containing a fluorescent dye compound as fluorescent-labelling nanobeads augmenting brightness as compared with the free fluorescent dye compound and wherein the fluorescence of the nanobeads is resistant to photobleaching.

Examples of the biochip of the present invention include a DNA chip, a protein chip and the like, as described above.

Generally, the DNA chip has nucleic acids (DNAs and RNAs), such as genome DNAs, placed and immobilized in the array shape on a surface of a substrate (e.g., silica substrate), and the information can be processed only by high-sensitivity analysis of the substrate surface (see, for example, JP-A-2004-004065, 2003-334079, and 2001-021558). It is possible to detect and quantify the target nucleic acids (DNAs and RNAs) contained in a sample (for example, cell extract or lysate) directly without tedious operation such as amplification by PCR by using it.

Generally, the protein chip has biomolecules (for example, antigen, antibody, ligand, receptor, nucleic acid) molecularly, specifically recognizing a target protein or the like (such as antigen, antibody, ligand, receptor, sugar, polysaccharide, or chemical substance) that are placed and immobilized in the array shape on the surface of a substrate (such as a silica substrate), and similarly to the DNA chip above, the information can be processed only after high-sensitivity analysis of the substrate surface (see, for example, JP-A-2005-287463 and 2003-130877).

The protein chip can be used in functional analysis, such as of an expression, an interaction, and a post-translational modification, of a target protein contained in a sample (for example, a blood serum, an urine, a culture solution), monitoring of protein purification, and the like.

Any one of commercially available biochip substrates including IntelliGene (registered trade name) TestARRAY Ver.4.0 (trade name, manufactured by TAKARA BIO INC.), GeneChip (registered trade name) Arrays (trade name, manufactured by Affymetrix, Inc.), and FAST (registered trade name) Quant Human Th1/Th2 Kit (trade name, manufactured by TAKARA BIO INC.) may be used as the substrate for the biochip of the present invention.

Hereinafter, the method of detecting or quantifying a target biomolecule (e.g., a target bioactive substance) will be described.

In the method of detecting or quantifying a target biomolecule of the present invention, the colloidal silica particles containing a fluorescent dye compound can be used as the fluorescent-labelling nanobeads which increase brightness as compared with the free fluorescent dye compound and wherein the fluorescence of the nanobeads is resistant to photobleaching. In particular, use of the biochip above is preferable.

In the method of detecting or quantifying a target biomolecule of the present invention, examples of the target biomolecules include, as the same as mentioned above, antigens, antibodies, DNAs, RNAs, sugars, polysaccharides, ligands, receptors, peptides, chemical substances, and the like, and, when the target biomolecule is a DNA or RNA, use of the DNA chip above is preferable. When the target biomolecule is a ligand, a protein such as receptor, a peptide, a sugar, a polysaccharide, or a chemical substance, use of the protein chip is preferable.

When the target biomolecule contained in a sample (for example, an optional cell extract, a lysate, a culture solution, or a solution, a buffer) is modified with a first molecular-recognition substance, the method of detecting or quantifying a target biomolecule of the present invention comprises the steps of:

making a target biomolecule-recognizing molecule immobilized on a substrate molecularly recognize the target biomolecule, making colloidal silica particles containing a fluorescent dye compound surface-modified with a second substance molecularly recognize the first molecular-recognition substance modifying the target biomolecule after molecular recognition with the first target biomolecule-recognizing molecule immobilized on the substrate, and detecting or quantifying the fluorescence from the silica particles on the substrate.

Typical examples of the target biomolecules modified with the first molecular-recognition substance include DNAs or RNAs modified with biotin or avidin, mouse IgG modified with biotin or avidin, mouse IgM modified with a maltose-binding protein, and the like.

Such a target biomolecule can be modified with such a first molecular-recognition substance, for example, according to the methods described in JP-A-9-154599 and 2003-522158, and the like.

In particular in the method of detection or quantification of the present invention, the combination of the first molecular-recognition substance and the second substance is preferably a combination selected from the group consisting of the following combinations (a) to (i):

(a) the first molecular-recognition substance is an antigen and the second substance is an antibody;

(b) the first molecular-recognition substance is an antibody and the second substance is an antigen;

(c) the first molecular-recognition substance is biotin, and the second substance is avidin or streptavidin;

(d) the first molecular-recognition substance is avidin or streptavidin and the second substance is biotin;

(e) the first molecular-recognition substance is a sugar or polysaccharide and the second substance is a sugar-bound protein binding to the sugar or polysaccharide specifically;

(f) the first molecular recognition reactive material is a sugar-bound protein and the second substance is a sugar or polysaccharide binding to the protein specifically;

(g) the first molecular-recognition substance is a ligand and the second substance is a receptor binding to the ligand specifically;

(h) the first molecular-recognition substance is a receptor and the second substance is a ligand binding to the receptor specifically; and (i) the first molecular-recognition substance is a chemical substance and the second substance is an antibody or peptide binding to the substance specifically.

When the colloidal silica particles containing a fluorescent dye compound are surface-modified with a substance specifically binding to or being adsorbed to the target biomolecule (hereinafter, referred to simply as "second target biomolecule-recognizing molecule"), the method of the present invention comprises the steps of:

making the first target biomolecule-recognizing molecule immobilized on a substrate molecularly recognize the target biomolecule in a sample, making the colloidal silica particles containing a fluorescent dye compound surface-modified with the second target biomolecule-recognizing molecule molecularly recognize the target biomolecule after molecular recognition with the first target biomolecule-recognizing molecule immobilized on the substrate, and detecting or quantifying the fluorescence from the silica particles on the substrate.

In particular, the method of detecting or quantifying a target biomolecule of the present invention may be a detection or quantification method in the double antibody sandwich system of using colloidal silica particles containing a fluorescent dye compound surface-modified with an antibody that recognizes the antibody recognizing site of the target biomolecule, as the fluorescence labelling antibody.

An example thereof is a method of detecting and quantifying a target human γ-interferon by the double antibody sandwich system of using an anti-human γ-interferon antibody as a substrate-immobilizing antibody and surface-modified colloidal silica particles containing a fluorescent dye compound surface-modified with an anti-human γ-interferon antibody, as a fluorescent-labelling antibody, that binds to another epitope different from the substrate-immobilizing antibody.

When the target biomolecule in a sample is labelled directly with the colloidal silica particles containing a fluorescent dye compound, the detecting or quantifying method of the present invention comprises the steps of:

making the biomolecule-recognizing molecule immobilized on a substrate molecularly recognize the target biomolecule labelled with the silica particles, and detecting or quantifying the fluorescence from the silica particles on the substrate.

In particular when the target biomolecule directly labelled is a DNA or RNA, use of a DNA chip is preferable, as described above; and it is possible to detect or quantify a DNA or RNA, by labelling the target DNA or target RNA in a sample with the colloidal silica particles containing a fluorescent dye compound, allowing the resulting particles to hybridize with the DNA or RNA immobilized on the substrate, and detecting or quantifying the label signal form the silica particle on the substrate.

When the target DNA or RNA is present only in a trace amount, it was not possible to detect it by using a DNA chip in the conventional method, without amplification for example by PCR and labelling with a fluorescent agent.

On the other hand, because the colloidal silica particles containing a fluorescent dye compound are used as high-brightness fluorescent-labelling nanobeads, there is no need for amplification by PCR or the like in the detecting or quantifying method of the present invention, even when the target DNA or RNA is present only in a trace amount.

The colloidal silica particle containing a fluorescent dye compound of the present invention, which is superior in brightness and photobleaching resistance, can be used in fluorescent labelling of any biomolecules or bioactive substances.

The colloidal silica particles containing a fluorescent dye compound of the present invention can be used as fluorescent-labelling nanobeads on a biochip, and use of the particles is effective in improving the data reproducibility of biochip assays drastically.

The fluorescent nano-material of the present invention is higher in brightness and superior in photobleaching resistance, and thus, can be used, for example, as fluorescent-labelling nanobeads labelling biomolecules and also as cosmetic materials.

The biochip of the present invention, which contains the colloidal silica particles containing a fluorescent dye compound as fluorescent-labelling nanobeads, is superior in sensitivity and data reproducibility.

The method of detecting and quantifying a biomolecule of the present invention can be used in analysis of any biomolecule or any bioactive substance, and is superior in the reproducibility of measured data.

EXAMPLES

The present invention will be described in more detail based on examples given below, but the invention is not meant to be limited by these.

Example 1

Preparation of Colloidal Silica Particles Containing a Fluorescent Dye Compound for a Biochip First, a method of preparing multiple colloidal silica particles containing a fluorescent dye compound having an average diameter of 30 nm or less will be described.
<Preparation of Colloidal Silica Particles Containing DY550 Modified with Streptavidin>

5.6 mg of DY550-NHS ester (trade name, manufactured by Dyomics GmbH) was dissolved in 1 ml of dimethylsulfoxide (DMSO). 1.3 µl of APS was added thereto, and the mixture was allowed to react at room temperature (25° C.) for one hour.

3.95 ml of ethanol, 20 µl of MPS, 1 ml of distilled water, and 100 µL of 28 mass % ammonia water were added to 50 µl of the reaction solution obtained, and the mixture was allowed to react at room temperature for 24 hours.

The reaction solution was ultrafiltered through YM-100 (trade name, manufactured by Millipore Corporation). The fluorescence silica particle dispersion after filtration was collected and ultrafiltered again then through YM-1 (trade name, manufactured by Millipore Corporation), and the fluorescence silica particle dispersion was concentrated to a total volume of one tenth. The concentrated solution was diluted with distilled water and ultrafiltered once again through YM-1. After concentration, the solution was diluted with distilled water and ultrafiltered; the operation was repeated four times, for removal of unreacted MPS, ammonia, and others contained in the fluorescence silica particle dispersion, to give 6 mg of fluorescence silica particles having an average diameter of 26 nm. The yield was approximately 40%.

Figure 1:
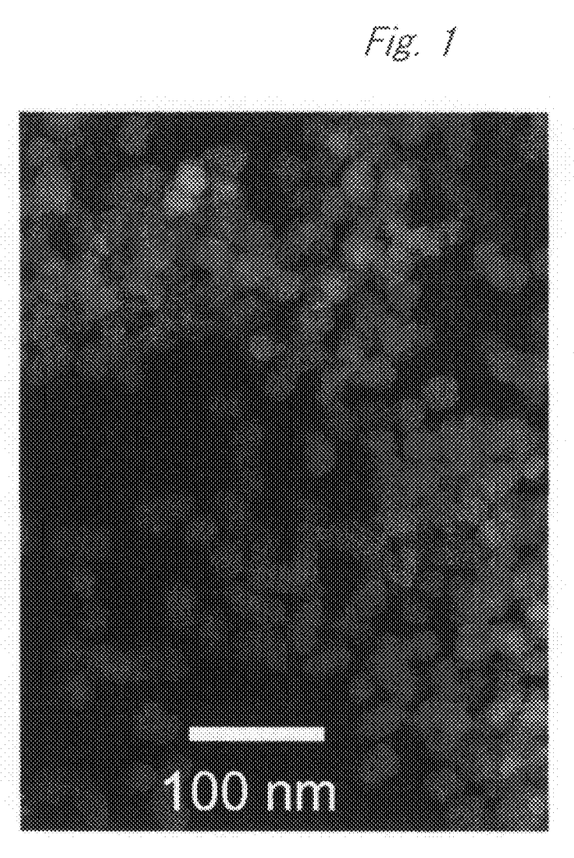
FIG. 1 is a TEM micrograph showing fluorescence silica particles obtained.

FIG. 1 is a TEM micrograph showing the fluorescence silica particles obtained. In the Figure, white objects represent the fluorescence silica particles obtained. Observation of the TEM micrograph shown in FIG. 1 confirms that the fluorescent colloidal silica particles were obtained. The average diameter is an average circle-equivalent diameter obtained by observing five different positions under TEM, determining an average circle-equivalent diameter of 50 randomly-selected silica particles in the TEM micrograph at each position, and determining the average thereof at the five positions.

After dialysis by a conventional method, 0.5 mg of streptavidin-maleimide (manufactured by SIGMA-ALDRICH Japan K.K.) was added to 1.5 mL of a 2 mg/mL dispersion of thiol-modified fluorescence silica particles, and the mixture was allowed to react at room temperature for two hours. After the reaction, unreacted streptavidin-maleimide was removed by dialysis by a conventional method, to give 3 mg of streptavidin-modified fluorescence colloidal silica fine particles containing DY550.
<Preparation of Streptavidin-Modified Fluorescent Colloidal Silica Particles Containing DY630>

Streptavidin-modified DY630-containing silica particles having an average diameter of 24 nm (6 mg) were obtained as the same manner as mentioned above, except that DY630-NHS ester (trade name, manufactured by Dyomics GmbH) was used as the dye. The yield was approximately 40%. The average diameter is an average circle-equivalent diameter obtained by observing five different positions under TEM, determining an average circle-equivalent diameter of 50 randomly-selected silica particles in the TEM micrograph at each position, and determining the average thereof at the five positions.

Example 2

DNA Chip Assay

Hereinafter, a method of a DNA chip assay by using the fluorescent silica nano-particles prepared in Example 1 will be described.
<Comparative Test on Photobleaching of a DNA Chip>

(1) A 30-base oligomer modified with biotin at the 5' terminal described below, which was used as the target biomolecule, was hybridized with a DNA chip in Hybridization Solution (trade name, manufactured by Nacalai Tesque, Inc.).

The DNA chip used was IntelliGene (registered trade name) TestARRAY Ver.4.0 (trade name, manufactured by TAKARA BIO INC.) carrying pUC19 DNA fragment arrayed and immobilized thereon.

A DNA having the sequence complementary to the pUC19 DNA fragment immobilized on IntelliGene TestARRAY Ver. 4.0, which has a sequence shown by the following SEQ ID No. 1, was prepared in a DNA synthesizer as the target biomolecule.

5'(biotin)-agcgtcgattttgtgatgctcgtcagggg-3' (SEQ ID No. 1)

(2) The DNA chip was washed with SSC (Solution buffer of sodium citrate); fluorescent labelling of each DNA chip was performed by using a streptavidin-modified DY550 molecule (manufactured by Dyomics GmbH) as Comparative Example or by using the streptavidin-modified DY550-containing fluorescence silica particles prepared in Example 1.

In the case of the labelling with the streptavidin-modified DY550 molecule, 200 μl of 200 μM streptavidin-modified DY550 molecule solution was used.

In the case of labelling with the streptavidin-modified DY550-containing fluorescence silica particles, 200 μl of 500 μg/ml streptavidin-modified DY550-containing fluorescence silica particle dispersion was used, and the reactions were carried out respectively in a phosphate-buffered sodium chloride solution (PBS) at 4° C. for 12 hours.

(3) The fluorescent-labelled DNA chip was analyzed in a DNA Microarray Scanner (trade name, manufactured by Agilent Technologies Japan, Ltd.) once to five times, and the decay in fluorescence intensity (photobleaching) was compared.

Figure 2:
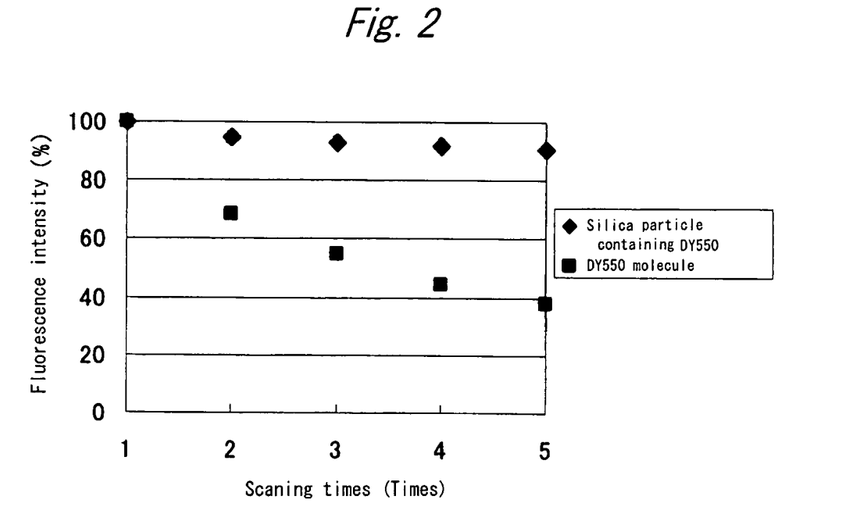
FIG. 2 is a graph showing the results in a comparative photobleaching test.

Results are summarized in FIG. 2.

As is apparent from FIG. 2, the DNA chip labelled with the DY550 molecule decayed in fluorescence intensity to less than 40% of the original value in five measurements in Comparative Example, while the DNA chip labelled with the DY550-containing fluorescence colloidal silica particle show decay only to approximately 90%.

The results above show that the fluorescent labelling with the fluorescence colloidal silica particle containing DY550 of the present invention, which is resistant to photobleaching, gives a DNA chip employing the fluorescence colloidal silica particles containing DY550 of the present invention superior in data reproducibility.

Thus, it is obvious that the fluorescence colloidal silica particles of the present invention can be used as fluorescent-labelling nanobeads for a biochip assay.

INDUSTRIAL APPLICABILITY

The colloidal silica particles containing a fluorescent dye compound of the present invention can improve data reproducibility drastically in assays using a biochip such as DNA chip, when used as fluorescence labelling nanobeads carrying a fluorescent dye compound introduced by a new method that compound shows fluorescence characteristics similar to those of Cy3 and Cy5 compatible as to detection and data in a general purpose detector for DNA chip, a so-called chip reader.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. Colloidal silica particles containing a fluorescent dye compound, composed of a silica particle comprising a silica component and a fluorescent dye compound chemically bound or adsorbed thereto, wherein the colloidal silica particles containing a fluorescent dye compound have an average diameter of 30 nm or less; and wherein the fluorescent dye compound is represented by any one of the following Formulae (1) to (3):

[Chemical formula 1]

Formula (1)

wherein each X independently represents $CR^3R^4$; each Y independently represents an atom or group selected from a hydrogen atom, hydrocarbon groups, and heteroatom-containing functional groups; either of $R^1$ or $R^2$ represents a group binding to the silica component covalently or a hydrocarbon group containing the group, and the other represents a hydrocarbon group that may have a functional group; each of $R^3$ and $R^4$ is a hydrogen atom or a hydrocarbon group, and at least one of them is a hydrocarbon group; and n is 1 or 2; and

[Chemical formula 2]

Formula (2)

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Chemically synthesized target DNA

<400> SEQUENCE: 1
agcgtcgatt tttgtgatgc tcgtcagggg         30

Formula (3)

wherein, $R^{11}$ and $R^{21}$ each represent a group binding throughout the silica component covalently;

and further wherein the surface of the silica particles is modified with a substance specifically binding to or adsorbed to a target biomolecule and fluorescence of the silica particles is resistant to photobleaching.

2. The colloidal silica particles containing a fluorescent dye compound according to claim 1, wherein at least one kind of the fluorescent dye compound is dispersed inside of each of the silica particles.

3. The colloidal silica particles containing a fluorescent dye compound according to claim 1, wherein a fluorescence of the silica particles is yellow fluorescence, orange fluorescence or red fluorescence.

4. The colloidal silica particles containing a fluorescent dye compound according to claim 1, wherein the silica particles each have amino, hydroxyl, thiol, carboxyl, maleimide and/or succinimidyl ester groups on a surface of each of the particles.

5. The colloidal silica particles containing a fluorescent dye compound according to claim 1,
wherein the colloidal silica particles containing a fluorescent dye compound are used for a biochip as fluorescent-labelling nanobeads,
wherein the nanobeads increase brightness as compared with a free fluorescent dye compound; and
wherein a fluorescence of the nanobeads that is resistant to photobleaching.

6. A fluorescent nano-material, comprising the colloidal silica particles containing a fluorescent dye compound according to claim 1.

7. A biochip, comprising the colloidal silica particles containing a fluorescent dye compound according to claim 1 as fluorescent-labelling nanobeads,
wherein the nanobeads increase brightness as compared with a free fluorescent dye compound; and
wherein a fluorescence of the nanobeads that is resistant to photobleaching.

8. A method of detecting or quantifying a biomolecule, comprising the steps of:
allowing a target biomolecule-recognizing molecule immobilized on a substrate to molecularly recognize a target biomolecule,
allowing colloidal silica particles containing a fluorescent dye compound composed of a silica particle comprising a silica component and a fluorescent dye compound, wherein the colloidal silica particles containing a fluorescent dye compound have an average diameter of 30 nm or less, wherein the fluorescent dye compound is dispersed inside of the whole silica particle including inside and in a region close to a surface of the silica particle, and wherein said colloidal silica particles have been surface-modified with a second substance that recognizes a first molecular-recognition substance to recognize the target biomolecule after molecular recognition by the target biomolecule-recognizing molecule immobilized on the substrate, and detecting or quantifying a fluorescence from the colloidal silica particles on the substrate; and wherein the target biomolecule in a sample is modified with the first molecular-recognition substance, wherein the fluorescent dye compound is represented by any one of the following Formulae (1) to (3):

Formula (1)

wherein each X independently represents $CR^3R^4$; each Y independently represents an atom or group selected from a hydrogen atom, hydrocarbon groups, and heteroatom-containing functional groups; either of $R^1$ or $R^2$ represents a group binding the silica component covalently or a hydrocarbon group containing the group, and the other represents a hydrocarbon group that may have a functional group; each of $R^3$ and $R^4$ is a hydrogen atom or a hydrocarbon group, and at least one of them is a hydrocarbon group; and n is 1 or 2; and Formula (2)

Formula (3)

wherein, $R^{11}$ and $R^{21}$ each represent a group covalently binding throughout the silica component.

9. The method of detecting or quantifying a biomolecule according to claim 8, wherein the combination of the first molecular-recognition substance and the second substance is any one combination selected from the group consisting of the following items (a) to (i):
(a) the first molecular-recognition substance is an antigen and the second substance is an antibody;
(b) the first molecular-recognition substance is an antibody and the second substance is an antigen;
(c) the first molecular-recognition substance is biotin and the second substance is avidin or streptavidin;
(d) the first molecular-recognition substance is avidin or streptavidin and the second substance is biotin;
(e) the first molecular-recognition substance is a sugar or polysaccharide and the second substance is a sugar-binding protein binding to the sugar or polysaccharide specifically;
(f) the first molecular-recognition substance is a sugar-binding protein and the second substance is a sugar or polysaccharide binding to the protein specifically;
(g) the first molecular-recognition substance is a ligand and the second substance is a receptor binding to the ligand specifically;
(h) the first molecular-recognition substance is a receptor and the second substance is a ligand binding to the receptor specifically; and
(i) the first molecular-recognition substance is a chemical substance and the second substance is an antibody or peptide binding to the substance specifically.

10. A method of detecting or quantifying a biomolecule using a double antibody sandwich system, comprising
binding an antibody to a surface of colloidal silica particles containing a fluorescent dye compound composed of a silica particle comprising a silica component and a fluorescent dye compound, wherein the colloidal silica particles containing a fluorescent dye compound have an average diameter of 30 nm or less, wherein the fluorescent dye compound is dispersed inside of the whole silica particle including inside and in a region close to a surface of the silica particle, and wherein the antibody recognizes an antibody recognition site of a target biomolecule,
exposing an antigen with affinity for the antibody to the antibody bound to the surface of the colloidal silica particles, and
detecting or quantifying fluorescence from the colloidal silica particles that are bound to the antigen and the antibody,
wherein the fluorescent dye compound is represented by any one of the following Formulae (1) to (3):

Formula (1)

wherein each X independently represents $CR^3R^4$; each Y independently represents an atom or group selected from a hydrogen atom, hydrocarbon groups, and heteroatom-containing functional groups; either of $R^1$ or $R^2$ represents a group binding the silica component covalently or a hydrocarbon group containing the group, and the other represents a hydrocarbon group that may have a functional group; each of $R^3$ and $R^4$ is a hydrogen atom or a hydrocarbon group, and at least one of them is a hydrocarbon group; and n is 1 or 2; and Formula (2)

Formula (3)

wherein, $R^{11}$ and $R^{21}$ each represent a group covalently binding throughout the silica component.

11. A method of detecting or quantifying a biomolecule, comprising the steps of:
labelling a target biomolecule in a sample with colloidal silica particles containing a fluorescent dye compound composed of a silica particle comprising a silica component and a fluorescent dye compound, wherein the colloidal silica particles containing a fluorescent dye compound have an average diameter of 30 nm or less, wherein the fluorescent dye compound is dispersed inside of the whole silica particle including inside and in a region close to a surface of the silica particle, and wherein said colloidal silica particles are,
allowing a target biomolecule-recognizing molecule immobilized on a substrate to molecularly recognize the target biomolecule labelled with the colloidal silica particles, and
detecting or quantifying a fluorescence form the colloidal silica particles on the substrate,
wherein the fluorescent dye compound is represented by any one of the following Formulae (1) to (3):

Formula (1)

wherein each X independently represents $CR^3R^4$; each Y independently represents an atom or group selected from a hydrogen atom, hydrocarbon groups, and heteroatom-containing functional groups; either of $R^1$ or $R^2$ represents a group binding the silica component covalently or a hydrocarbon group containing the group, and the other represents a hydrocarbon group that may have a functional group; each of $R^3$ and $R^4$ is a hydrogen atom or a hydrocarbon group, and at least one of them is a hydrocarbon group; and n is 1 or 2; and Formula (2)

Formula (3)

wherein, $R^{11}$ and $R^{21}$ each represent a group covalently binding throughout the silica component.

12. The method of detecting or quantifying a biomolecule according to claim 8, wherein the target biomolecule is an antigen, an antibody, a DNA, a RNA, a sugar, a polysaccharide, a ligand, a receptor, a peptide or a chemical substance.

13. The method of detecting or quantifying a biomolecule according to claim 10, wherein the target biomolecule is an antigen, an antibody, a DNA, a RNA, a sugar, a polysaccharide, a ligand, a receptor, a peptide or a chemical substance.

14. The method of detecting or quantifying a biomolecule according to claim 11, wherein the target biomolecule is an antigen, an antibody, a DNA, a RNA, a sugar, a polysaccharide, a ligand, a receptor, a peptide or a chemical substance.

15. A method of detecting or quantifying a DNA or RNA, comprising the steps of:
labelling a target DNA or RNA in a sample with colloidal silica particles containing a fluorescent dye compound composed of a silica particle comprising a silica component and a fluorescent dye compound, wherein the colloidal silica particles containing a fluorescent dye compound have an average diameter of 30 nm or less,
allowing the above-labelled target DNA or RNA to hybridize with a DNA or RNA immobilized on a substrate, and detecting or quantifying a fluorescence label signal from the colloidal silica particles on the substrate,
wherein the fluorescent dye compound is represented by any one of the following Formulae (1) to (3):

Formula (1)

wherein each X independently represents $CR^3R^4$; each Y independently represents an atom or group selected from a hydrogen atom, hydrocarbon groups, and heteroatom-containing functional groups; either of $R^1$ or $R^2$ represents a group binding the silica component covalently or a hydrocarbon group containing the group, and the other represents a hydrocarbon group that may have a functional group; each of $R^3$ and $R^4$ is a hydrogen atom or a hydrocarbon group, and at least one of them is a hydrocarbon group; and n is 1 or 2; and Formula (2)

Formula (3)

wherein, $R^{11}$ and $R^{21}$ each represent a group covalently binding throughout the silica component.

16. The method of detecting or quantifying a biomolecule according to claim 8, wherein two or more kinds of target biomolecules are detected or quantified simultaneously.

17. The method of detecting or quantifying a biomolecule according to claim 10, wherein two or more kinds of target biomolecules are detected or quantified simultaneously.

18. The method of detecting or quantifying a biomolecule according to claim 11, wherein two or more kinds of target biomolecules are detected or quantified simultaneously.

19. The method of detecting or quantifying a biomolecule according to claim 13, wherein two or more kinds of target biomolecules are detected or quantified simultaneously.

\* \* \* \* \*